(12) United States Patent
Carver et al.

(10) Patent No.: US 7,482,161 B2
(45) Date of Patent: Jan. 27, 2009

(54) PREPARATION OF A RED BLOOD CELL COMPONENT FOR A HEMATOLOGY CONTROL

(75) Inventors: Franklin J. Carver, Benicia, CA (US); Lorraine Granier, San Ramon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 11/777,864

(22) Filed: Jul. 13, 2007

(65) Prior Publication Data

US 2008/0026468 A1    Jan. 31, 2008

Related U.S. Application Data

(60) Provisional application No. 60/807,585, filed on Jul. 17, 2006.

(51) Int. Cl.
*G01N 33/96* (2006.01)
*G01N 33/48* (2006.01)

(52) U.S. Cl. .................. 436/10; 436/8; 436/17; 436/63; 436/128; 436/174; 436/176; 435/2

(58) Field of Classification Search ............ 436/8, 436/10, 17, 63, 108, 128, 174, 175, 176; 435/2
See application file for complete search history.

(56) References Cited

U.S. PATENT DOCUMENTS

| | | | | | |
|---|---|---|---|---|---|
| 3,873,467 | A | * | 3/1975 | Hunt | 436/10 |
| 3,973,913 | A | * | 8/1976 | Louderback | 436/11 |
| 4,579,824 | A | * | 4/1986 | Louderback et al. | 436/10 |
| 4,777,139 | A | * | 10/1988 | Wong et al. | 436/18 |
| 6,146,901 | A | * | 11/2000 | Carver et al. | 436/174 |
| 6,403,377 | B1 | * | 6/2002 | Ryan et al. | 436/8 |
| 6,653,063 | B2 | * | 11/2003 | Carver et al. | 435/2 |
| 2005/0227359 | A1 | * | 10/2005 | Ortiz et al. | 436/10 |
| 2006/0194191 | A1 | * | 8/2006 | Zhang et al. | 435/2 |

FOREIGN PATENT DOCUMENTS

GB            1509539        *  5/1978

* cited by examiner

*Primary Examiner*—Maureen M Wallenhorst
(74) *Attorney, Agent, or Firm*—Townsend and Townsend and Crew LLP.; M. Henry Heines

(57) ABSTRACT

Red blood cells from a vertebrate are treated to make them effective components of a hematology control, allowing the control to be used for detecting all blood cell components, including white blood cells and platelets. The treatment includes the use of a fixative under limited conditions of concentration and exposure time, and the resulting red blood cells are stable but lysable in a hematology instrument and have a reduced tendency to form particulates.

10 Claims, No Drawings

PREPARATION OF A RED BLOOD CELL COMPONENT FOR A HEMATOLOGY CONTROL

CROSS-REFERENCE TO RELATED APPLICATION

This application claims benefit from U.S. Provisional Patent Application No. 60/807,585, filed Jul. 17, 2006, the contents of which are incorporated herein by reference in their entirety.

BACKGROUND OF THE INVENTION

1. Field of the Invention

This invention resides in the field of control materials for hematology instrumentation, with particular attention to red blood cell components of the control materials.

2. Description of the Prior Art

Hematology instruments for the analysis of blood components and chemistry have been used for many years, during which time the accuracy and sensitivity of these instruments have progressively advanced. The early forms of hematology instrumentation have thus been replaced by relatively complex machines that analyze the discrete components of blood based upon the intricate and subtle characteristics of each component.

The most recent iteration in automated hematology instrumentation has been the multi-part analysis of human white cells, in addition to the detection of red blood cells and platelets. White cell populations typically include lymphocytes, monocytes, neutrophils, basophiles, and eosinophils. The methods for blood cell analysis involve detection of the electrical and optical properties of each type of blood cell. A typical instrument will count and size red blood cells and platelets independently of the white cell component. To count white cells, it is necessary to destroy the red blood cells using a detergent such as a quaternary ammonium salt, leaving the white cells for counting and sizing.

The Beckman-Coulter™ five-part white cell analysis instrument uses several distinct technologies, variously based on electrical impedance, conductance (a DC mathematical manipulation that uses a low-voltage DC measurement), Rf (radio frequency) modulation, and laser technology which includes light scatter and light absorption. The Rf measurement is typically used with the DC low frequency measurement to create a parameter called opacity which is a calculation of Rf divided by DC. Instruments by other manufacturers, such as Abbott Diagnostics™, Bayer™, and TOA™ Medical Electronics, use a combination of electrical impedance, DC conductance and/or laser technology, Rf, depolarized 90° angle light scatter, and/or light absorption. Although the basic types of electronic technology may appear the same, each manufacturer has a unique implementation for the instrument hardware and software that is required to analyze blood cells. The individual implementations of this technology by the various manufacturers have resulted in a wide array of reagents and methodology for each specific instrument of each manufacturer, thereby increasing the complexity and expense of their use. No single reagent or methodology exists that can be used with a plurality of instruments.

To ensure the reliability and accuracy of hematology instruments, regulatory authorities require the use of blood controls to verify the integrity of the instruments. The optimal control contains particles that represent all of the cellular elements of fresh blood, together with a synthetic plasma, which is a liquid suspending medium artificially formulated to simulate human plasma. A synthetic plasma typically contains components that are the same as, or function in the same manner as, components of native plasma. These components include inorganic salts, organic and/or inorganic buffers, and a viscous material for maintaining a homeostasis similar to that maintained by plasma proteins. The manufacturer of a control provides all of the critical values such as cell count, cell size, and cell type. The control material should have sufficient shelf life to allow it to be used for days, weeks, or months, thereby ensuring the consistency of instrument performance over time.

The method for preparing a hematology control is dependent on the hardware and software design of the specific instrument in which the control is to be used, as well as the requirements for extended shelf life. Blood controls consist of an RBC component which is typically washed human red blood cells suspended in a synthetic plasma. The red blood cells are accompanied by one or more particles that will appear to the instrument as white blood cell sub-populations. While the white cell controls can be human white cells, are animal red cells that have been stabilized with a cross-linking agent to prevent them from being destroyed by a detergent are used as an alternative. Particles in blood control products that can serve as controls for human white cells, red blood cells, or platelets on a Coulter™-type instrument may not be effective for other instruments, such as those manufactured by Abbott Laboratories™, Bayer™, or TOA™ Medical Electronics. Moreover, because these particles are usually modified forms of various types of blood cells, they do not behave like living native fresh blood cells. For example, human white cells fixed with a cross-linking agent like glutaraldehyde may behave like a neutrophil on an Abbott™ instrument and like cellular debris on a Coulter™ instrument. Also, specially treated and cross-linked red blood cells from non-mammalian vertebrates may appear as mononuclear cells on one type of hematology instrument and as lymphocytes on another. The red blood cell component of a hematology control may serve well on a number of instruments for verifying numerical and chemical values such as count and hemoglobin content, as well as physical characteristics such as size and shape, and yet the values, particularly those of physical characteristics as mean cell volume (MCV), size distribution (RDW, i.e., red cell distribution width), and cell shape, can vary widely among different instruments. In addition, a red blood cell preparation may be read by one type of instrument as containing debris in the platelet and/or white cell counting regions and as containing no such debris by another type of instrument. For example, the red cell preparation in the Hematology (C) product manufactured by Bio-Rad Laboratories, Inc., has a high platelet background on the Bayer H1-E Hematology Instrument. On the Abbott CELL-DYN 4000 instrument, the same red blood cell preparation shows interference in the optical platelet and white cell regions. No platelet or white cell interference appears on the Abbott CELL-DYN 3000 series or 1000 series instruments. The red cell preparation used for the Bio-Rad Hematology (C) product shows no platelet or white cell interference on Coulter instruments as the Coulter Model MaxM but does show platelet and white cell interference on the Abbott CELL-DYN 4000 instrument.

The prior art contains reports of the addition of certain analytes to the suspending medium of a blood control to improve the performance of the red blood cell component in the control by modifying physical characteristics of the component and preventing the formation of particulate debris. Ryan et al., in U.S. Pat. No. 6,403,377 B1, teach the addition of lipoprotein to improve the size characteristics of white cell components and the addition of an anti-oxidant to prevent red blood cell lysis. The use of lipoprotein to increase the volume of the leukocyte components is likewise disclosed by Young, U.S. Published Patent Application No. US 2005/0221497 A1. In contrast to Ryan et al., the lipoprotein in Young serves to allow proper lysing of the red blood cells by a detergent used in the Coulter instrumentation. Young also describes the need for a non-ionic detergent in a blood control to further aid in red blood cell lysis without compromising the integrity of the white cell surrogates used in the blood control.

Fixation of red blood cells has been shown to be an effective method of providing non-lysable particles suitable for use as leukocyte analogs. Hunt, in U.S. Pat. No. 3,873,467, describes a fixation method for producing leukocyte analogs using human red blood cells. Ryan et al. above describe the stabilization of red blood cells using cross-linking agents. Cells that have been fixed by these methods are resistant to mechanical stress such as that induced by sonication. Young et al. above describe detailed fixation procedures for producing a number of different types of leukocyte analogs. Other fixation processes for leukocyte analogs are disclosed by Carver et al., in U.S. Pat. Nos. 6,146,901, 6,514,763B2, 4,704,364, and 5,380,664. All of the patents and published patent applications cited in this section and elsewhere throughout this specification are incorporated herein by reference.

SUMMARY OF THE INVENTION

An object of the present invention is to provide a method for preparing red blood cells from a vertebrate source for use in a hematology blood control product, and particularly a method that is sufficiently flexible to compensate for the different technologies employed by hematology instrument manufacturers. The present invention allows one to customize a process using the method described herein to achieve a hematology control that uniquely meets the specification of a chosen hematology instrument.

It also is an object of the present invention to provide a method to prepare a hematology blood control from human red blood cells without the need for plasma cholesterol or lipoprotein to enhance red blood cell lysability.

It is a further object of the present invention to provide a hematology blood control that has a red blood cell component that does not require a surfactant or other lysis promoter in the control itself to improve the lysability of the red blood cell component in the hematology instrument.

It is a further object of the present invention to provide a hematology blood control that has a red blood cell component that is fixed with cross-linking agents that minimize or prevent the formation of particulates that interfere in the platelet and white cell counting regions.

It is a further object of the present invention to provide a hematology blood control that has a red blood cell component that (a) is fixed with crosslinking agents that provide a uniform size and shape on multiple instrument types and that (b) still maintains lysability in the presence of mild detergents used with conventional hematology instruments known and used in the art that discriminate white cell sub-populations.

It is a further object of the present invention to provide a hematology blood control that can be utilized on a plurality of instruments made by different manufacturers.

It is yet another object of the present invention to provide a hematology blood control that can be prepared easily and inexpensively.

To accomplish these and other related objectives, the red blood cell component used in the practice of the present invention is achieved by treating (i.e., preconditioning) red blood cells from a vertebrate source, i.e., non-nucleated mammalian red blood cells, with a low concentration of a fixative for a relatively short period of time. The fixative can be any of various substances known for use as tissue stabilizing agents, and the preconditioning procedure includes an incubation of the cells with the fixative long enough to crosslink the cells while leaving the cells lysable in the instrument. The cells once pre-conditioned are combined with components representing other blood cell types to complete the composition of the control, and the control is then processed in the instrument in the same manner as a blood sample that is sought to be analyzed. The results of the analysis are then compared to the known composition, i.e., the known blood cell distribution, of the control, and the comparison serves as a check on the condition of the instrument to verify that the instrument is in condition for use on an actual sample. The preconditioning process is a limited fixation process and differs from the typical prior art fixation of red blood cells for blood control products, in which the cells are made resistant to lysis by the detergents used in hematology instruments. In the present invention, the fixation of red blood cells is done in such a manner that the fixed cells are lysable under prescribed instrument verification conditions to allow both the red blood cells and the white blood cells, and any other blood components as desired, in the control product to be counted. The fixation is nevertheless sufficient to provide the red blood cells with count stability, physical stability (i.e., stable volume and shape), and particle integrity and to prevent the formation of particulates that interfere with the analysis of white blood cells and/or platelets. The process also results in red blood cells that register both cell size and count uniformly across multiple instrument technologies including, but not limited to, electrical (e.g. impedance) and optical (i.e. light scatter) technologies.

DETAILED DESCRIPTION OF THE INVENTION AND PREFERRED EMBODIMENTS

Fixatives that can be used in the practice of the present invention vary widely in molecular structure. One group of such fixatives are organic dialdehydes, and preferably those that contain two terminal aldehyde groups separated by a linking group that includes a backbone chain containing at least two carbon atoms. The backbone chain can also contain heteroatoms such as O atoms and N atoms, but backbones that are particularly preferred are saturated alkylenes (i.e., divalent alkyl chains) of 2 to 6 carbon atoms. The linking group can also contain branched groups bonded to the backbone as side chains, such as —OH, —NH$_2$, —CH$_2$, —OCH$_3$, and homologs and analogs of such groups, but particularly preferred linking groups are straight-chain alkylenes with no side chains. Examples of organic dialdehydes that meet the latter description are glutaraldehyde and butane-1,4-dial. One source of butane-1,4-dial is HISTOCHOICE®, a tissue fixative commercially available from Amresco Inc., Solon, Ohio, USA, and identified by its supplier as being disclosed in Camiener, U.S. Pat. No. 5,429,797, issue date Jul. 4, 1995. Components of HISTOCHOICE other than butane-1,4-dial, according to the product literature, are glyoxal, sodium chloride, and zinc sulfate. Another group of fixatives useful in the practice of this invention are diazolidinyl urea, imidazolidinyl urea, dimethylol urea, dimethylol-5,5-dimethylhydantoin, 2-bromo-2-nitropropane-1,3-diol, quaternary adamantine, 4-hydroxymethyl-1-aza-3,7-dioxabicyclo[3.3.0]octane, and 5-hydroxymethyl-1-aza-3,7-dioxabicyclo[3.3.0]octane. Among this group, diazolidinyl urea and imidazolidinyl urea are preferred. Diazolidinyl urea is available from Streck Laboratories, Inc., La Vista, Nebr., USA, as Streck Tissue Fixative, in which diazolidinyl urea is the main active ingredient with 2-bromo-2-nitropropane-1,3-diol, zinc sulfate, and a small amount of formaldehyde as further ingredients.

The conditions for preconditioning of the RBCs, while generally mild compared to prior art uses of the same fixatives, are adjustable within certain ranges. When preconditioning is performed at room temperature or in general at temperatures within the range of from about 15° C. to about 25° C. (59° F. to 77° F.), for example, the fixative concentration may range from about 0.1% to about 1.0% (on a weight/volume basis, i.e., grams per mL×100), and the incubation time may range from about 0.5 hour to about 4 hours. By contrast, when preconditioning is performed at a reduced temperature such as, for example, about 2° C. to about 8° C. (36° F. to 44° F.), the fixative concentration may range from about 0.05% to about 0.25% (on a weight/volume basis), and the incubation time may range from about 16 hours to about 48 hours.

The fixative treatment can be done in a single stage or in multiple stages. A first stage can, for example, include treatment at a moderate temperature (15° C. to 25° C.) for a short period of time (0.5 hour to 4 hours) at a very low fixative concentration such as 0.001% to 0.25% at room temperature or 15-25° C., while the second stage can include treatment for the same exposure time and temperature but at a higher concentration such as 0.1% to 1.0%, or at a reduced temperature (2° C. to 8° C.) for a longer period of time (16 hours to 48 hours). Further processing procedures will be apparent to those skilled in the art. Cell conditioning subsequent to the fixative exposure can, for example, be achieved by incubation in simulated plasma in the absence of a fixative for about 7 days to about 30 days at about 2° C. to about 8° C., and various wash steps with conventional wash solutions and stabilizing steps with conventional plasma substitutes can be used between treatments.

Red blood cells that can be used in the practice of this invention are non-nucleated mammalian red blood cells, such as those from humans, cattle, sheep, goats, and non-avian livestock in general. Human red blood cells are preferred. In addition, any of the various different kinds of red blood cells can be preconditioned in the practice of this invention. This includes Type A, Type B1, and Type B2.

As noted above, the remaining components of the control can be conventional components of hematology controls, including white blood cell components and platelet components. The white blood cell component can be fixed vertebrate red blood cells or non-biological particles such as microbeads of polystyrene, polyvinyltoluene, or styrenedivinylbenzene. Microparticles from biological sources can also be used; examples are latex particles and plant pollen. Still further materials are those disclosed in Carver et al., U.S. Patent Application Publication No. US 2002/0022269 A1, publication date Feb. 21, 2002, and references cited therein. The platelet component can be red blood cells obtained from a goat shrunken to the size of human blood platelets by suspension of the cells in a series of aqueous hypertonic salt solutions of successively increasing concentrations of the salt until the desired size range is achieved. Examples of suitable salt solutions are solutions of dialkali metal salts of the naphthol-disulfonic acids, such as the dipotassium salt of 2-naphtol-6,8-disulfonic acid and the disodium salt of 2-naphthol-3,6-disulfonic acid. Other salt solutions and other methods of obtaining platelet components are known in the art and can be used here as well.

The artificial or simulated plasma that is used as the suspending medium for the control can be any of the various liquid preparations known for this purpose. Suitable preparations will be isosmotic to mammalian blood and will contain components that are identical or similar to native plasma, or that function in a manner identical or similar to native plasma. The components include inorganic salts, organic and inorganic buffers, and a viscous material for maintaining homeostasis such as mammalian albumin or a synthetic alternative such as polyethylene glycol. One or more antibiotics such as ProClin P150, Amikacin, gentamycin, penicillin, and tetracycline are also typically included. Examples of synthetic plasmas available by commercial suppliers are HESPAN® (DuPont Pharmaceuticals, Wilmington, Del., USA), PENTASPAN® (DuPont Pharmaceuticals), MACRODEX® (Pharmacia, Inc., Piscataway, N.J., USA), RHEOMACRODEX® (Pharmacia, Inc.), and HEXTEND® (BioTime, Inc., Berkeley, Calif., USA). A simulated plasma is typically an aqueous solution of electrolytes at physiological concentration plus a macromolecular oncotic agent and a biological buffer. In addition to its use as the suspending medium for the hematology control product, the artificial plasma can also be used as a suspending medium for stabilization of the cells after conditioning. The choice of a particular artificial plasma is in some cases made with particular hematology instruments in mind, since the artificial plasma can have an effect on the presence of particles in the white blood cell and platelet counting regions specific to the instrument manufacturer technology.

As noted above, it is known in the art that hematology instruments from different manufacturers utilize different blood cell counting technologies. Thus, partially degraded red blood cells or fragments of red blood cells that are present in a blood sample may appear (and be counted) in the white blood cell region of the readout of some instruments, the platelet region, or both, while in other instruments these partially degraded cells and fragments do not appear in these regions. In addition, the electronic impedance and/or optical properties of normal or abnormal fresh red blood cells or preserved red blood cells may be such that intact red blood cells or degraded cells (e.g. red blood cell ghosts and/or fragments) may behave differently depending on the instrument design. For example, abnormal fresh red blood cells may be present in the WBC counting region using an Abbott Cell-Dyne CD4000 due to the resistance of the red blood cell to a lytic agent. The same abnormal red blood cell will not show or may have a different signature (particle distribution) on a Coulter instrument. With the present invention, the modification of the red blood cells for use in a control can be performed under different conditions depending on whether the instrument in which the control is to be used will show any change in electronic or optical properties of intact red blood cells or any change in the electronic or optical properties of partially degraded cells or fragments as blood components other than red blood cells. The exposure time, temperature, and fixative concentration can thus be adjusted to achieve the degree of modification needed to avoid this misrepresentation of the cell type distribution in the instrument readout, and yet to still allow lysis of the red blood cell component according to the protocol of the instrument. Information on how the various instruments operate and differ is readily known among skilled and experienced hematologists and in some cases is supplied by the manufacturer, and the selection of optimal conditions is readily made on this basis. Such information is also readily determinable by routine investigation, by running on the instrument a standard suspension of red blood cells that have been washed in citrate and suspended in an artificial plasma, and observing the readout to note where any electronically or optically modified intact cells or partially degraded cells and fragments appear.

The components needed for a typical red blood cell preparation procedure as an illustration of the present invention are as follows:

Packed human red blood cells typically collected at blood donor sites
Fluid for washing the packed human red blood cells
Fluid for primary fixing of the washed packed human red blood cells
Fluid for washing the primary fixed cells
Fluid for suspending the washed primary fixed cells
Optional: Fluid for secondary fixing of the washed primary fixed cells, and fluid for washing the secondary fixed cells
Fluid for storing the primary (or secondary) washed fixed cells The following examples, in which all percents are on a weight/volume basis, are offered only for purposes of illustration.

EXAMPLE 1

The following example illustrates the preparation of a Type A red blood cell component for use in a commercial blood control product that provides uniform red blood cell values across multiple hematology technology platforms. The procedure used in this example resulted in a control product that does not create interference from scattered particles in non-RBC regions (i.e., white blood cell and platelet analysis regions). This example was optimized for use on Bayer 5-part instruments with example profiles from the Bayer (formerly Technicon) H1-E instrument. The procedure prevents the formation of particulate matter in the lower platelet counting region yet provides a red blood cell component for a blood control that has consistent RBC parameters between instrument types. This is an important distinction for the Bayer instruments due to the unique method used by these instruments for evaluating RBC volume, distribution width, and cellular hemoglobin content.

The procedure was as follows:
1. Add donor site packed RBC's to a 1 L centrifuge bottle and add an isosmotically balanced citrate wash solution to a count of $2\times10^6/\mu L$ to $4\times10^6/\mu L$, preferably $3\times10^6/\mu L$.
2. Centrifuge for 10-30 minutes, preferably 20 minutes, at 2,000-4,000 RPM, preferably at 3,000 RPM, aspirate supernatant, and fill with citrate wash solution to a count of $2\times10^6/\mu L$ to $4\times10^6/\mu L$, preferably $3\times10^6/\mu L$.
3. Repeat the citrate wash, resuspend with citrate wash solution to a count of $2\times10^6/\mu L$ to $4\times10^6/\mu L$, preferably $3\times10^6/\mu L$.
4. Pour resuspended RBC's into a second 1 L bottle containing sufficient glutaraldehyde to equal 1% of a stock solution of 24% glutaraldehyde.
5. Fix at room temperature for 0.5-4 hours, preferably 2 hours.
6. Wash as above with citrate wash solution.
7. Resuspend in artificial plasma for 12-20 hours, preferably 16 hours.
8. Centrifuge for 10-30 minutes, preferably 20 minutes, at 2,000-4,000 RPM, preferably 3,000 RPM, aspirate supernatant, and fill with artificial plasma solution to a red blood cell count of $2\times10^6/\mu L$ to $5\times10^6/\mu L$, preferably $2\times10^6/\mu L$.
9. Store at $1\times10^6/\mu L$ to $3\times10^6/\mu L$, preferably, $2\times10^6/\mu L$, at 2-8° C. for 7-30, preferably 21, days for cell conditioning.
10. Aspirate supernatant to an RBC count required for the final blood control product which ranges from about 0.5 to about $7\times10^6/\mu L$ depending on the target value. For example, a level 1 would be from 0.5 to $4\times10^6/\mu L$, a level 2 from 2 to $5\times10^6/\mu L$, and a level 3 control from 3 to $7\times10^6/\mu L$.
11. Add a white blood cell component(s) (WBC) in the form of fixed vertebrate white blood cells, WBC analogs in the form of fixed vertebrate RBC's and/or in the form of other particle types as latex particles and pollen.
12. Add a platelet component, for example a native mammalian platelet prepared in an anticoagulant or a platelet analog prepared from an animal source. The preferred platelet component is from an animal source as goat red blood cells as disclosed in Hunt, U.S. Patent No. U.S. Pat. No. 4,179,398.
13. Adjust cell counts and cell sizes as required for the manufacture of blood controls with normal and abnormal hematological conditions.

For purposes of comparison, the prior art conditions for the use of glutaraldehyde as a fixative for tissue fixation include contacting the tissue with glutaraldehyde at a glutaraldehyde concentration of approximately 1% for about 24 hours. The control produced by the procedure described above was used on the Bayer H1-E and Advia 120 instruments, where it did not result in the formation of particles in the lower platelet region. The control produced a crescent-shaped particle distribution in the optical platelet region on the Abbott CD4000 and debris in the CD4000 WBC scattergram. This caused WBC (white blood cell) and RBC (red blood cell) system errors in the CD4000.

The control product used in this example was tested on six commercial hematology instruments for red blood cell count (RBC), hemoglobin (HGB), and mean cell volume (MCV), and samples of fresh blood were also tested on the same six instruments. The results for fresh blood are shown in Table I and the results for the control are shown in Table II.

TABLE I

| | Fresh Blood | | |
|---|---|---|---|
| Instrument | RBC | HGB | MCV |
| Coulter STK-R | 5.03 | 15.8 | 88.3 |
| Sysmex-KX21 | 4.99 | 15.6 | 88.1 |
| Abbott CD1600 | 5.55 | 16.4 | 84.9 |
| Biocode Hycel-Xenia | 5.34 | 17.5 | 87.8 |
| Coulter MAXM | 5.22 | 15.4 | 88.0 |
| Bayer Advia 120 | 4.95 | 14.9 | 83.7 |
| Mean | 5.18 | 15.9 | 86.8 |
| Standard Deviation | 0.2 | 0.9 | 2.0 |
| Coefficient of Variance | 4.5% | 5.8% | 2.3% |

TABLE II

| | Type A1 Control | | |
|---|---|---|---|
| Instrument | RBC | HGB | MCV |
| Coulter STK-R | 4.33 | 14.48 | 94.66 |
| Sysmex-KX21 | 4.29 | 14.28 | 91.70 |
| Abbott CD1600 | 4.41 | 13.52 | 95.16 |
| Biocode Hycel-Xenia | 4.42 | 14.46 | 98.58 |
| Coulter MAXM | 4.38 | 13.44 | 92.12 |
| Bayer Advia 120 | 4.46 | 13.82 | 83.28 |

TABLE II-continued

|  | Type A1 Control | | |
| --- | --- | --- | --- |
| Instrument | RBC | HGB | MCV |
| Mean | 4.38 | 14.0 | 92.6 |
| Standard Deviation | 0.1 | 0.5 | 5.2 |
| Coefficient of Variance | 1.4% | 3.3% | 5.6% |

The data in Table II show a close correlation of the results between the different instruments, particularly in the mean cell volume, indicating the universality of the control. The Bayer Advia, for which the preparation was made, showed a similar MCV bias with fresh blood and the Type A1 Control.

EXAMPLE 2

This example illustrates a procedure for preparing a Type B1 red blood component preparation that provides uniform red blood cell values across multiple hematology technology platforms with the near absence of scattered particles in non-RBC (i.e., white blood cell and platelet analysis) regions. The procedure in this example was optimized for use on the Abbott CD4000 5-part instrument. The procedure prevents the formation of particulate matter in the optical platelet and optical WBC counting regions yet provides a red blood cell component for a blood control that has consistent RBC parameters between instrument types. This is an important distinction for the Abbott instrument due to methods used for evaluating RBC, platelet, and WBC parameters. The procedure outlined below is for Type B1 RBC's and involves a primary fixation using an ultra-low short exposure of glutaraldehyde followed by a moderate concentration of a second fixation (secondary fix) using a non-glutaraldehyde fixative, in this case HISTOCHOICE®, which is a fixative that is relatively safe in terms of environmental concerns and has an effect that is distinct from that achieved with fixatives such as formaldehyde and glutaraldehyde.

The procedure was as follows.
1. Add donor site packed RBC's to a 1 L centrifuge bottle and add an isosmotically balanced citrate wash solution to a count of $2 \times 10^6/\mu L$ to $4 \times 10^6/\mu L$, preferably $3 \times 10^6/\mu L$.
2. Centrifuge for 10 to 30 minutes, preferably 20 minutes, or until packed at 2,000 to 4,000 RPM, preferably 3,000 RPM, aspirate supernatant, and fill with citrate wash solution to a count of $2 \times 10^6/\mu L$ to $4 \times 10^6/\mu L$, preferably $3 \times 10^6/mL$.
3. Repeat the citrate wash, resuspend red blood cells with citrate wash solution to a count of $2 \times 10^6/\mu L$ to $4 \times 10^6/\mu L$, preferably $3 \times 10^6/\mu L$.
4. Pour resuspended RBC's into a second 1 L bottle containing sufficient glutaraldehyde to equal 0.005 to 1.0%, preferably 0.01%, of a stock solution of 24% glutaraldehyde, resulting in a final glutaraldehyde concentration of 0.001% to 0.25%, preferably 0.0025%.
5. Fix at room temperature for 0.5-4 hours but preferably 2 hours.
6. Wash as above with citrate wash solution and repeat one more time.
7. Resuspend in an artificial plasma for 12 to 20 hours, preferably 16 hours.
8. Centrifuge for 20 minutes at 2,000 to 4,000, preferably 3,000 RPM, aspirate supernatant, and fill with artificial plasma suspending media solution to a count of $2 \times 10^6/\mu L$ to $4 \times 10^6/\mu L$, preferably $3 \times 10^6/\mu L$.
9. Add sufficient HISTOCHOICE to a second container to equal a final HISTOCHOICE concentration of 0.1% to 5%, preferably 1%.
10. Pour the washed glutaraldehyde primary fixed and washed cells into the bottle containing HISTOCHOICE.
11. Store at 2-8° C. for 16-48 hours, preferably 24 hours.
12. Centrifuge at 2,000 to 4,000, preferably 3,000 RPM for 10 to 30 minutes, preferably 20 minutes, and aspirate the supernatant.
13. Wash as above with artificial plasma suspending solution.
14. Repeat the washing procedure two more times.
15. Store at $1 \times 10^6/\mu L$ to $3 \times 10^6/\mu L$, preferably $2 \times 10^6/\mu L$ at 2-8° C. for 7-30 but preferably 21 days for cell conditioning.
16. Centrifuge for 10-30 minutes, preferably 20 minutes, at 2,000-4,000 RPM, preferably 3,000 RPM, aspirate supernatant, and fill with artificial plasma solution to a red blood cell count of $2 \times 10^6/\mu L$ to $5 \times 10^6/\mu L$, preferably $2 \times 10^6/\mu L$.
17. Store at $1 \times 10^6/\mu L$ to $3 \times 10^6/\mu L$, preferably, $2 \times 10^6/\mu L$, at 2-8° C. for 7-30, preferably 21, days for cell conditioning.
18. Aspirate supernatant to an RBC count required for the final blood control product which ranges from about 0.5 to about $7 \times 10^6/\mu L$ depending on the target value. For example, a level 1 would be from 0.5 to $4 \times 10^6/\mu L$, a level 2 from 2 to $5 \times 10^6/\mu L$, and a level 3 control from 3 to $7 \times 10^6/\mu L$.
19. Add a white blood cell component(s) (WBC) in the form of fixed vertebrate white blood cells, WBC analogs in the form of fixed vertebrate RBC's and/or in the form of other particle types as latex particles and pollen.
20. Add a platelet component, prepared as in Example 1.
21. Adjust cell counts and cell sizes as required for the manufacture of blood controls with normal and abnormal hematological conditions.

The resulting red blood cell preparation formed particles in the lower platelet region on the Bayer H1-E and Advia 120 instruments. The preparation did not have particles that fit the optical platelet region on the Abbott CD4000. No RBC or WBC system errors were observed on the Abbott instrument such as those that typically occur with legacy RBC formulations. For purposes of comparison, the prior art conditions for the use of HISTOCHOICE include contacting the cells with the fixative at a fixative concentration of approximately 3-4% for 1 to 3 days.

The control product used in this example was tested on the seven commercial hematology instruments as in Example 1, for red blood cell count, hemoglobin, and mean cell volume. Fresh blood, different from that used in Example 1, was also tested on the seven instruments. The results for fresh blood are shown in Table III while those for the control are shown in Table IV.

TABLE III

|  | Fresh Blood | | |
| --- | --- | --- | --- |
| Instrument | RBC | HGB | MCV |
| Coulter STK-R | 5.79 | 15.8 | 77.9 |
| ABX Spirit | 5.80 | 15.6 | 79.5 |
| Abbott CD1600 | 5.91 | 16.1 | 80.0 |
| Abbott CD1700 | 5.59 | 15.5 | 81.2 |
| Abbott CD3500 | 5.80 | 15.9 | 79.2 |
| Abbott CD4000 | 5.76 | 15.8 | 79.8 |
| Bayer H1-E | 5.67 | 15.7 | 80.6 |

TABLE III-continued

| | Fresh Blood | | |
|---|---|---|---|
| Instrument | RBC | HGB | MCV |
| Mean | 5.76 | 14.0 | 79.7 |
| Standard Deviation | 0.10 | 0.5 | 1.05 |
| Coefficient of Variance | 1.8% | 3.3% | 1.3% |

TABLE IV

| | Type B1 RBC | | |
|---|---|---|---|
| Instrument | RBC | HGB | MCV |
| Coulter STK-R | 4.25 | 13.7 | 88.6 |
| ABX Spirit | 4.18 | 13.5 | 88.4 |
| Abbott CD1600 | 4.19 | 13.5 | 89.6 |
| Abbott CD1700 | 4.28 | 13.8 | 87.9 |
| Abbott CD3500 | 4.29 | 13.8 | 88.9 |
| Abbott CD4000 | 4.12 | 13.6 | 86.8 |
| Bayer H1-E | 4.22 | 13.8 | 87.0 |
| Mean | 4.38 | 13.7 | 88.2 |
| Standard Deviation | 0.1 | 0.14 | 1.01 |
| Coefficient of Variance | 1.4% | 1.0% | 1.1% |

The data in Table IV show a close correlation between the results from the different instruments, particularly in the mean cell volume, indicating the universality of the control.

EXAMPLE 3

This example likewise illustrates a procedure for preparing a Type B2 red blood component preparation that provides uniform red blood cell values across multiple hematology technology platforms, again with the near absence of scattered particles in non-RBC (i.e. white blood cell and platelet analysis) regions. Like Example 2, this example was optimized for use on the Abbott CD4000 5-part instrument. The procedure allows the formation of particulate matter in the optical platelet region but prevents the formation of particular matter in the optical WBC counting regions, yet provides a red blood cell component for a blood control that has consistent RBC parameters between instrument types. The fixative used in this procedure is HISTOCHOICE®.

The procedure was as follows.
1. Add donor site packed RBC's to a 1 L centrifuge bottle and add an isosmotically balanced citrate wash solution to a count of $2 \times 10^6/\mu L$ to $4 \times 10^6/\mu L$, preferably $3 \times 10^6/\mu L$.
2. Centrifuge for 10-30 minutes, preferably 20 minutes, or until packed at 2,000 RPM to 4,000 RPM, preferably 3,000 RPM, aspirate supernatant, and fill with citrate wash solution to a count of $2 \times 10^6/\mu L$ to $4 \times 10^6/\mu L$, preferably $3 \times 10^6/\mu L$.
3. Repeat the citrate wash, resuspend with citrate wash solution to a count of $2 \times 10^6/\mu L$ to $4 \times 10^6/\mu L$, preferably $3 \times 10^6/\mu L$.
4. Resuspend in an artificial plasma suspending media for 12 to 20 hours, preferably 16 hours.
5. Centrifuge for 10 to 30 minutes, preferably 20 minutes, at 2,000 RPM to 4,000 RPM, preferably 3,000 RPM, aspirate supernatant, and fill with artificial plasma suspending media solution to a count of $2 \times 10^6/\mu L$ to $4 \times 10^6/\mu L$, preferably $3 \times 10^6/\mu L$.
6. Add sufficient HISTOCHOICE to a second container to equal a final concentration of 0.1% to 5% but preferably 1% HISTOCHOICE.
7. Pour the washed cells into the bottle containing HISTOCHOICE.
8. Store at 2-8° C. for 16-48 hours, preferably 24 hours.
9. Centrifuge at 2,000 RPM to 4,000 RPM, preferably 3,000 RPM for 10 minutes to 30 minutes, preferably 20 minutes, and aspirate the supernatant.
10. Wash as above with artificial plasma suspending solution.
11. Repeat the washing procedure two more times.
12. Store at $1 \times 10^6/\mu L$ to $3 \times 10^6/\mu L$, preferably $2 \times 10^6/\mu L$ at 2-8° C. for 7-30 but preferably 21 days for cell conditioning.
13. Aspirate supernatant to the desired RBC count.
14. Add a white blood cell component(s) (WBC) in the form of fixed vertebrate white blood cells, fixed vertebrate RBC's as WBC analogs, and/or other particles such as latex and pollen.
15. Add a platelet component.
16. Adjust cell counts and cell sizes as required for the manufacture of blood controls with normal and abnormal hematological conditions.

The resulting preparation formed particles in the lower platelet region on the Bayer H1-E and Advia 120 instruments. In the WBC scattergram of the Abbott 4000, particles appear in the optical platelet region and no debris appears.

The foregoing is offered for purposes of illustration. Further variations, modifications, and substitutions that fall within the scope of the invention will be readily apparent to those skilled in the art.

What is claimed is:

1. A method for verifying the accuracy of a hematology instrument that analyzes a sample of mammalian blood containing red blood cells by a process that includes lysing said red blood cells in said instrument and that determines relative amounts of different types of blood cells in said sample, said method comprising:

analyzing in said instrument according to said process a blood control having a known composition and comprising a red blood cell component, a white blood cell component, and a platelet component, of known relative amounts, suspended in a simulated plasma, said red blood cell component consisting of non-nucleated Type B1 mammalian red blood cells that have been pre-conditioned by incubation with butane-1,4-dial at a concentration of about 0.05% to about 2.5% (weight/volume) for a period of time of about 16 hours to about 48 hours at a temperature of about 2° C. to about 8° C., to crosslink said red blood cells while leaving said red blood cells lysable in said instrument, and comparing the results of said analysis with said known composition.

2. The method of claim 1 wherein said blood control is devoid of lysis promoters.

3. A method for verifying the accuracy of a hematology instrument that analyzes a sample of mammalian blood containing red blood cells by a process that includes lysing said red blood cells in said instrument and that determines relative amounts of different types of blood cells in said sample, said method comprising:

analyzing in said instrument according to said process a blood control having a known composition and comprising a red blood cell component, a white blood cell component, and a platelet component, of known relative amounts, suspended in a simulated plasma, said red blood cell component consisting of non-nucleated mammalian Type B2 red blood cells that have been preconditioned by incubation with, glutaraldehyde at a concentration of about 0.001% to about 0.25% (weight/ volume) for a period of time of about 0.5 hour to about 4 hours at a temperature of about 15° C. to about 25° C., followed by butane-1,4-dial at a concentration of about 0.05% to about 2.5% (weight/volume) for a period of time of about 16 hours to about 48 hours at a temperature of about 2° C. to about 8° C., and comparing the results of said analysis with said known composition.

4. The method of claim 3 wherein said blood control is devoid of lysis promoters.

5. A blood control comprising a red blood cell component, a white blood cell component, and a platelet component, of known relative amounts, suspended in a simulated plasma, said red blood cell component consisting of non-nucleated Type B1 mammalian red blood cells that have been pre-conditioned by incubation with butane-1,4-dial at a fixative concentration of about 0.05% to about 2.5% (weight/volume) for a period of time of about 16 hours to about 48 hours at a temperature of about 2° C. to about 8° C., to crosslink said red blood cells while leaving said red blood cells lysable in a hematology instrument.

6. The blood control of claim 5 wherein said blood control is devoid of lysis promoters.

7. The blood control of claim 5 wherein said non-nucleated mammalian red blood cells, after said incubation with said butane-1,4-dial, have been further pre-conditioned by incubation in simulated plasma in the absence of a fixative for about 7 days to about 30 days at about 2° C. to about 8° C.

8. A blood control comprising a red blood cell component, a white blood cell component, and a platelet component, of known relative amounts, suspended in a simulated plasma, said red blood cell component consisting of non-nucleated mammalian Type B2 red blood cells that have been pre-conditioned by incubation with glutaraldehyde at a concentration of about 0.001% to about 0.25% (weight/volume) for a period of time of about 0.5 hour to about 4 hours at a temperature of about 15° C. to about 25° C., followed by butane-1,4-dial at a concentration of about 0.05% to about 2.5% (weight/volume) for a period of time of about 16 hours to about 48 hours at a temperature of about 2° C. to about 8° C., to crosslink said red blood cells while leaving said red blood cells lysable in a hematology instrument.

9. The blood control of claim 8 wherein said blood control is devoid of lysis promoters.

10. The blood control of claim 8 wherein said non-nucleated mammalian red blood cells, after said incubation with said glutaraldehyde and butane-1,4-dial, have been further pre-conditioned by incubation in simulated plasma in the absence of a fixative for about 7 days to about 30 days at about 2° C. to about 80° C.

* * * * *